US009089663B2

(12) United States Patent
Rosenbaum et al.

(10) Patent No.: US 9,089,663 B2
(45) Date of Patent: Jul. 28, 2015

(54) PERCUTANEOUS ACCESS DEVICE

(75) Inventors: Joanna Lynn Rosenbaum, Bloomington, IN (US); Andrea Lawrence, Clarkston, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 504 days.

(21) Appl. No.: 13/536,421

(22) Filed: Jun. 28, 2012

(65) Prior Publication Data
US 2014/0000627 A1 Jan. 2, 2014

(51) Int. Cl.
*A61M 11/00* (2006.01)
*A61M 16/04* (2006.01)

(52) U.S. Cl.
CPC ....... *A61M 16/0472* (2013.01); *A61M 16/0434* (2013.01); *A61M 16/0497* (2013.01)

(58) Field of Classification Search
CPC ..................... A61M 16/0465; A61M 16/0434; A61M 16/0429; A61M 16/04; A61M 16/0427
USPC ........................... 128/207.14, 207.15, 207.29
See application file for complete search history.

(56) References Cited

U.S. PATENT DOCUMENTS

| 4,946,446 A | 8/1990 | Vadher ........................ 604/198 |
| 5,374,250 A | 12/1994 | Dixon ........................... 604/110 |
| 5,653,230 A | 8/1997 | Ciaglia et al. ............ 128/207.15 |
| 6,572,584 B1 | 6/2003 | Shaw et al. ................. 604/110 |
| 6,637,435 B2 | 10/2003 | Ciaglia et al. ............ 128/207.29 |
| 7,036,510 B2 | 5/2006 | Zgoda et al. ............ 128/207.29 |
| 7,351,224 B1 | 4/2008 | Shaw ........................... 604/110 |
| 2006/0081260 A1 | 4/2006 | Eells et al. ............... 128/207.29 |
| 2009/0320834 A1* | 12/2009 | Cuevas et al. ............ 128/200.26 |
| 2011/0290245 A1* | 12/2011 | Cuevas et al. ............ 128/200.26 |
| 2012/0180787 A1* | 7/2012 | Bosel ....................... 128/200.26 |
| 2013/0025588 A1* | 1/2013 | Bosel ....................... 128/200.26 |

* cited by examiner

*Primary Examiner* — Steven Douglas
(74) *Attorney, Agent, or Firm* — Brinks Gilson & Lione

(57) ABSTRACT

A device for providing access through a body wall of a patient to a target site includes a hollow tube having a first large diameter segment and a second small diameter segment. A first distally tapered portion joins the first segment and the second segment, and a second distally tapered portion is distal of the second segment. A first lumen extends through the tube, and a second lumen extends from a proximal portion of the tube to the second segment. A needle received in the first lumen is deployable for piercing the body wall. A port is provided along the second segment in communication with the second lumen, and a balloon is disposed along the second segment at the port. The balloon is inflatable to a diameter at least as large as the first segment diameter for dilating an opening in the body wall.

20 Claims, 6 Drawing Sheets

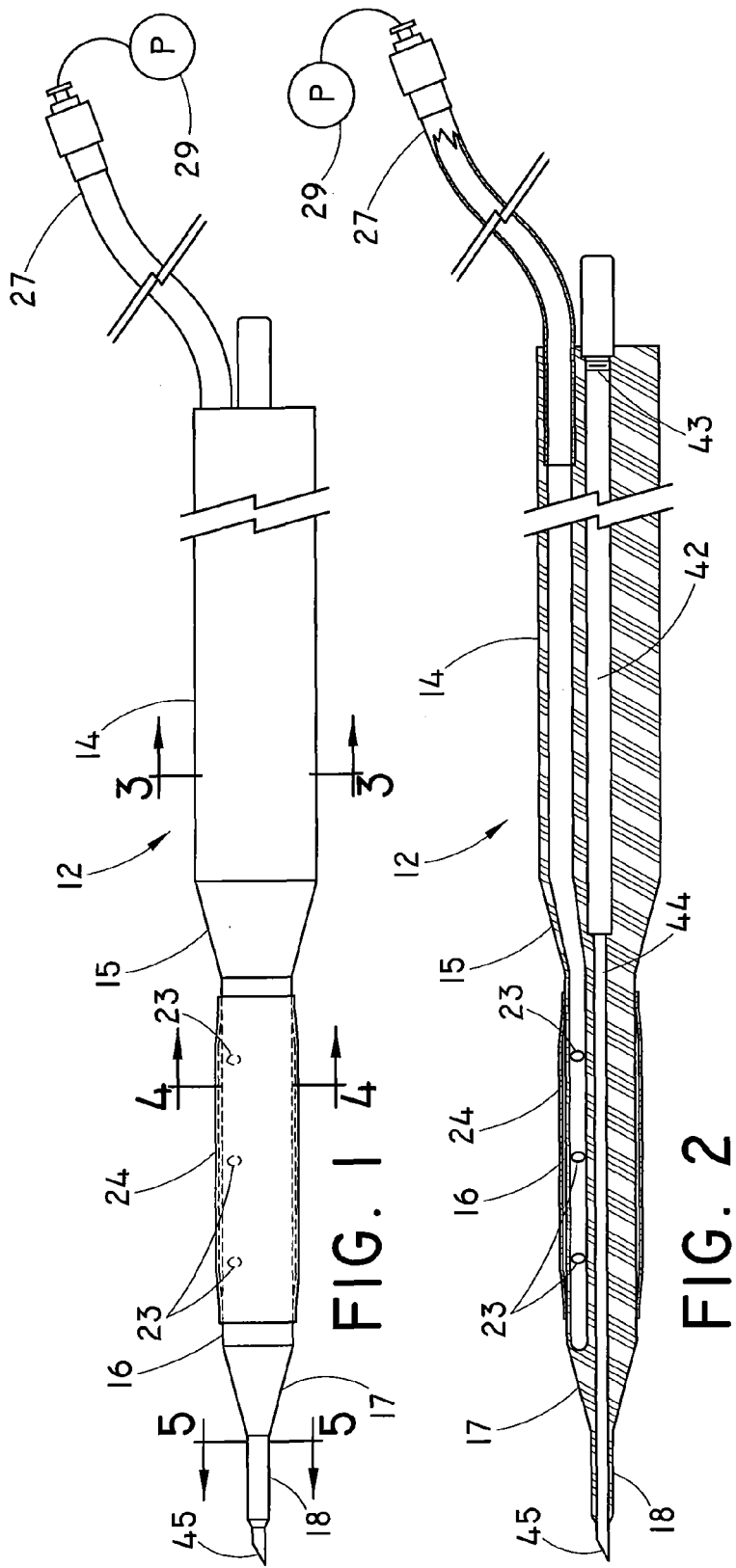

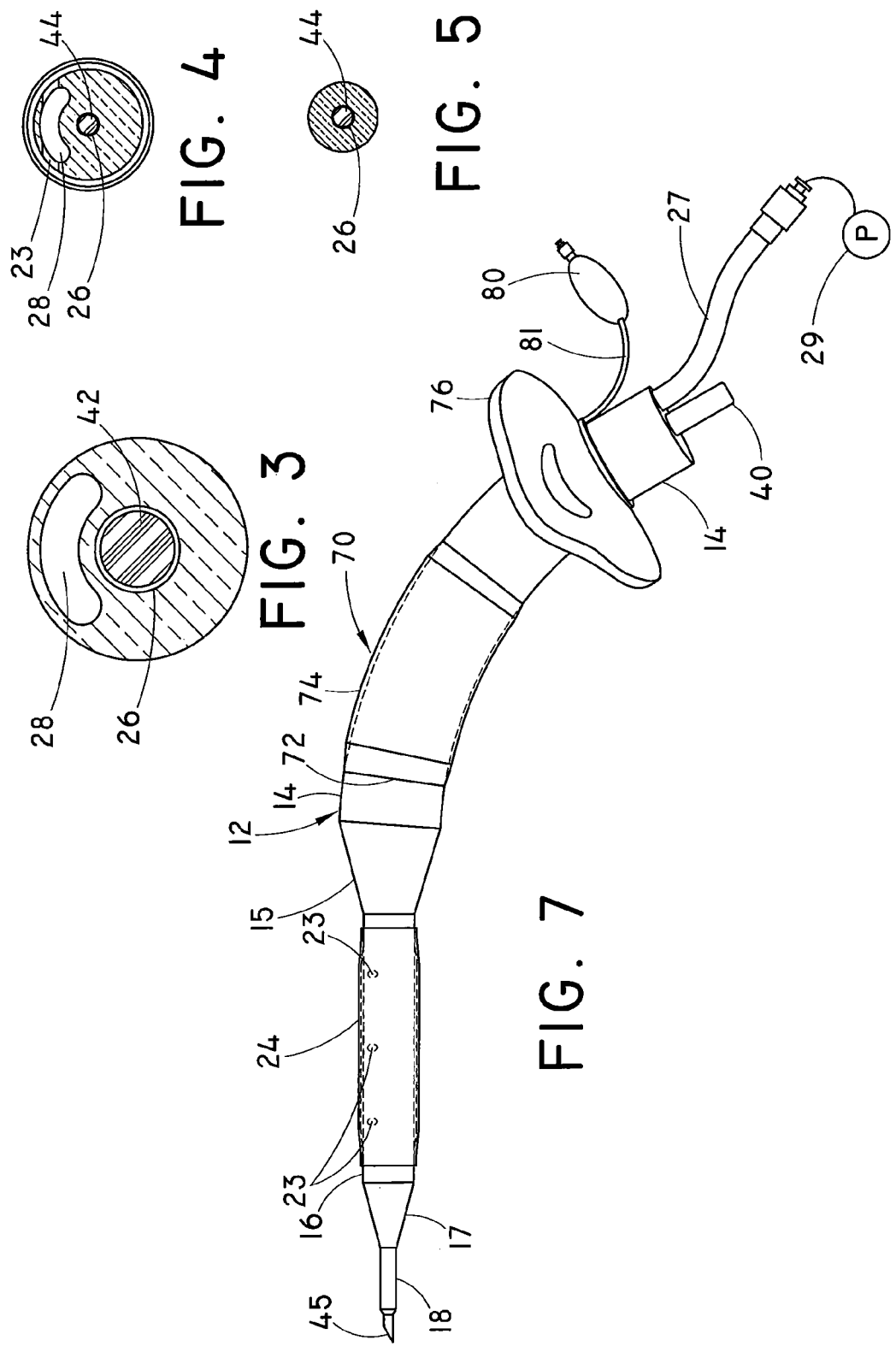

PERCUTANEOUS ACCESS DEVICE

BACKGROUND

1. Technical Field

This invention relates generally to a device for providing access to a target site within the body of a patient, and more particularly, to a medical device for providing percutaneous access to a patient's air passageway.

2. Background Information

The restoration of an adequate air passageway is the first critical step in maintaining the ability of a seriously ill or injured patient to breathe, or in performing resuscitation on a patient unable to breathe. Endotracheal intubation (the insertion of a breathing tube through the nostrils or mouth and into the trachea itself) is the preferred method for establishing an air passageway when the trachea, nostrils and/or mouth are free of obstruction. When such obstruction is present, however, endotracheal intubation may not be possible. In such instances, airflow must be established through an alternate passageway in the body of the patient.

The most direct way to provide an air passageway under these circumstances is to form an opening in the tracheal wall, and once formed, to maintain the opening by positioning a tracheostomy tube through the opening. Conventional tracheostomy tubes generally comprise a curved tubular member having an open distal end extending into the trachea, and an inflatable cuff to provide a seal between the tracheal wall and the tracheostomy tube.

Several methods and devices are known for forming or enlarging an opening in a tracheal wall. Each method is subject to its own advantages and drawbacks. For example, tracheostomy and cricothyrotomy procedures have been performed by using a scalpel to make a rather large incision in the neck for insertion of the tracheostomy tube. Such procedures entail a high degree of surgical skill to perform successfully, particularly since it is vital to locate and avoid unintentional severing of the blood vessels in the area. These procedures can even require the surgeon to cut through several blood vessels and ligate (tie) them to the trachea, in order to achieve an adequately large opening. The length of time needed to perform these procedures (often, on the order of half an hour) is poorly suited for emergency treatment, when prompt restoration of the air passageway is critical. Moreover, the use of a scalpel to fully form a relatively large opening may cause undue trauma to the tissues surrounding the opening, and can result in the formation of an unduly large or oversized opening in the soft tissue of the neck.

To minimize such trauma, it is desirable to initially incise only a small opening, and thereafter enlarge the opening with further dilation. For example, one technique for dilating an opening includes the use of a wire guide to facilitate the introduction of a dilator into the trachea. This technique involves the insertion of a needle and an over-the-needle catheter into the trachea. The needle is removed and the catheter replaced with a wire guide. A tapered, elongated, tubular dilator is positioned over the wire guide and introduced into the trachea. Even though intended to be performed in an emergency situation, this technique entails the sequential manipulation of several devices by the physician, which is time consuming and complicates the procedure.

Another procedure eliminates the use of the catheter and involves placing a wire guide through the needle itself. The opening formed by the needle is then dilated by the use of a device having a handle and a nose, the nose extending laterally from the axis of the handle. The nose has two jaws that spread apart for separating the tissue surrounding the opening, and the device is introduced into the trachea by positioning the elongated, tapered nose over the wire guide. While this type of device offers more powerful dilation than is possible with elongated tubular dilators, a problem with the device is that the unguarded nose must be inserted into the trachea with precision, and must be manipulated at an angle, in order to avoid perforating the posterior tracheal wall.

Another prior art technique for dilating an opening is the use of a tapered, elongated, tubular dilator, or a series of tapered dilators having increasingly larger diameters. Although such dilators are effective for forming a suitably-sized opening in the tracheal wall, each dilator presents a pointed distal end to the posterior tracheal wall when introduced into the trachea. The risk of injury to the trachea is compounded by the toughness of the tracheal membrane, which resists the introduction of medical devices. Introducing these elongated dilators may require the application of considerable force. Although a hydrophilic coating may be applied to the dilator to reduce the amount of force required to insert the dilator, a physician must still exert a downward force to push the dilator into the trachea, and yet avoid puncturing the posterior tracheal wall.

Another prior art technique involves the use of a balloon catheter to radially expand an opening formed in the tracheal wall. This device permits the enlargement of an opening without risk of perforating the rear of the trachea by providing a polymeric inflatable balloon at the distal end of the catheter. The device is inserted over a previously positioned wire guide such that the uninflated balloon spans the tracheal wall. The balloon is thereafter inflated to radially dilate the opening in the tracheal wall.

Although the recited devices may be effective for dilating an opening, such methods may be complex, and often require several procedural steps to carry out the procedure. In addition, numerous separate components must often be manipulated to carry out the procedure. This increases the time, complexity, and cost of the procedure.

It would be desirable to provide a device for use in gaining access to a target site of the patient, such as the patient's airway, that enables the access procedure to be carried out in a relatively short period of time, and that does not require the use of numerous individual components for carrying out the procedure.

BRIEF SUMMARY

The present invention addresses the problems of the prior art. In one form thereof, the invention comprises a device for providing access through a body wall of a patient to a target site. The device includes a hollow tubular member having a proximal end and a distal end. A first segment of the hollow tubular member has a first diameter, and a second segment has a second diameter, wherein the first diameter is greater than the second diameter. A first distally tapered portion provides a transition between the first segment and the second segment, and a second distally tapered portion is distal of the second segment. The hollow tubular member has a pair of lumens therealong. A first lumen extends from a proximal portion of the tubular member to the distal end, and a second lumen extends from a proximal portion of the tubular member to the second segment. At least one port is provided along the second segment in communication with the second lumen. An inflatable member, such as a balloon, is disposed along the second segment at the port. The inflatable member is configured and arranged such that upon inflation thereof the inflatable member has a diameter at least as large as the first diameter.

In another form thereof, the invention comprises an assembly for providing an airway through the tracheal wall of a patient. A device for forming an opening in the tracheal wall comprises a hollow tubular member having a proximal end and a distal end. A first segment has a first diameter, and a second segment has a second diameter, wherein the first diameter is greater than the second diameter. A first distally tapered portion provides a transition between the first segment and the second segment, and a second distally tapered portion is distal of the second segment. The hollow tubular member has a pair of lumens therealong. A first lumen extends to the distal end, and a second lumen extends to the second segment. At least one port along the second segment communicates with the second lumen. An inflatable member is disposed along the second segment at the at least one port. The inflatable member is dimensioned such that upon inflation the inflatable member has a diameter at least as large as a diameter of a tracheostomy tube carried on the first segment. A needle is received in the first lumen. The needle has a piercing tip selectively deployable and retractable through the first lumen for piercing the tracheal wall. A tracheostomy tube is carried on the first segment for positioning along the tracheal wall.

In still another form thereof, the invention comprises a method for providing an airway through the tracheal wall of a patient. An assembly is positioned at a site along the tracheal wall for insertion therethrough. The assembly comprises a hollow tubular member having a proximal end and a distal end, a first segment having a first diameter, and a second segment having a second diameter, the first diameter being greater than the second diameter. A first distally tapered portion provides a transition between the first segment and the second segment, and a second distally tapered portion is distal of the second segment. The hollow tubular member has a pair of lumens therealong, wherein a first lumen extends from a proximal portion of the tubular member to the distal end, and a second lumen extends to the second segment. At least one port is disposed along the second segment in communication with the second lumen. A needle is received in the first lumen such that a distal tip of the needle is selectively deployable from the distal end of the tubular member. An inflatable balloon is disposed along the second segment and covering the at least one port. A conduit communicates with the second lumen for transmission of an inflation fluid through the second lumen and the at least one port to an interior of the inflatable balloon. A tracheostomy tube is carried by the first segment. The needle distal tip is deployed from the first lumen such that the needle tip pierces the tracheal wall at the site, thereby forming an opening to the trachea. The assembly is advanced along the opening such that the second distally tapered portion dilates the opening, and the balloon is positioned across the tracheal wall. An inflation fluid is conveyed through the second lumen and the at least one port for inflating the balloon, such that the opening is dilated to a diameter of the balloon upon inflation. The assembly is advanced into the dilated opening such that the tracheostomy tube is positioned across the tracheal wall, and the hollow tubular member is withdrawn from the opening and the positioned tracheostomy tube.

BRIEF DESCRIPTION OF THE DRAWINGS

FIG. 1 is a side view of an embodiment of a percutaneous access device according to an embodiment of the present invention, with the balloon in an uninflated condition;

FIG. 2 is a side view of the percutaneous access device of FIG. 1, partially in section;

FIG. 3 is a transverse sectional view of the percutaneous access device of FIG. 1, taken along line 3-3 of FIG. 1;

FIG. 4 is a transverse sectional view of the percutaneous access device of FIG. 1, taken along line 4-4 of FIG. 1;

FIG. 5 is a transverse sectional view of the percutaneous access device of FIG. 1, taken along line 5-5 of FIG. 1;

FIG. 6 is a side view of a needle for use with the percutaneous access device of FIG. 1;

FIG. 7 is a perspective view showing a tracheostomy tube loaded on the percutaneous access device of FIG. 1;

DETAILED DESCRIPTION OF THE DRAWINGS AND THE PRESENTLY PREFERRED EMBODIMENTS

Figure 8:
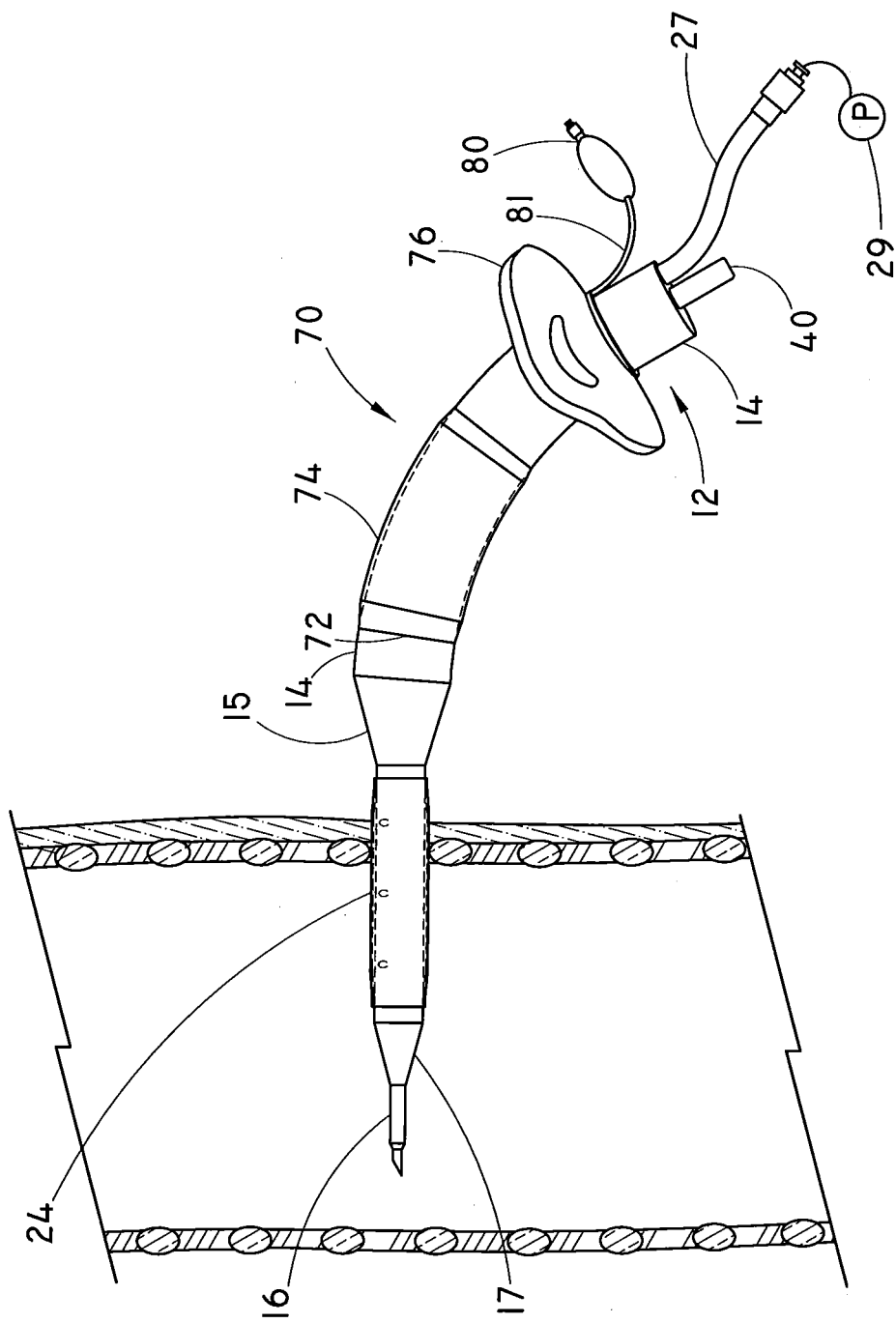
FIGS. 8-10 illustrate various steps during use of the percutaneous access device for positioning a tracheostomy tube across the tracheal wall of a patient.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the percutaneous access device, as well as the axial ends of various component features. The term "proximal" is used in its conventional sense to refer to the end of the device (or component) that is closest to the medical professional during use of the device. The term "distal" is used in its conventional sense to refer to the end of the device (or component) that is initially inserted into the patient, or that is closest to the patient during use.

One embodiment of a percutaneous access device 10 is illustrated in FIGS. 1 and 2. Percutaneous access device 10 comprises a hollow tubular member 12 having a first segment 14 having a first diameter, a second segment 16 having a second diameter, and a third segment 18 having a third diameter. A distally tapered portion 15 provides a transition between first segment 14 and second segment 16, and a distally tapered portion 17 provides a transition between second segment 16 and third segment 18.

In one form, first segment 14 may have a length between about 40 and 100 mm, and preferably, about 80 mm. The diameter of first segment 14 may be between about 20 and 38 French (6.7 and 12 mm), and preferably about 26 French (8.7 mm). Second segment 16 may have a length between about 15 and 55 mm, and preferably, about 45 mm. The diameter of second segment 16 may be between about 10 and 20 French (3.3 and 6.7 mm), and preferably about 14 French (4.7 mm). Third segment 18 may have a length between about 3 and 12 mm, and preferably, about 6 mm. The diameter of third segment 18 may be between about 6 and 9 French (2 and 3 mm), and preferably about 7 French (2.3 mm).

Tapered portion 15 may taper along a length of about 25 mm, and provides a generally smooth transition between first segment 14 and second segment 16. Tapered portion 17 may taper along a length of about 12 mm, and provides a generally smooth transition between second segment 16 and third segment 18. Although the embodiment shown in FIGS. 1 and 2 includes three segments as shown and described, third segment 18 is optional. When this segment is not present, tapered portion 17 may taper to the distal end of the tubular hollow member 12.

An inflatable balloon 24 is positioned along a length of segment 16. Preferably, the balloon 24 has a generally cylindrical shape upon inflation (FIG. 9). The diameter of balloon 24 upon inflation is selected in view of the size of the opening to be formed in a body wall, such as the tracheal wall. The diameter of the balloon upon inflation is at least as large, and preferably larger, than the diameter of first segment 14. When balloon 24 is used to dilate the tracheal wall for placement of a tracheostomy tube, the inflated diameter of balloon 24 is preferably at least as large as the diameter of the tracheostomy tube. In many cases, the diameter of the inflated balloon is between about 30 and 40 French (10 and 13.4 mm), such as about 38 French (12.7 mm). Balloon 24 has a length sufficient to span the wall of the body structure (e.g., the tracheal wall) being dilated. See, e.g., FIG. 8. Typically, balloon 24 has a length between about 10 and 50 mm.

As shown in FIGS. 3-5, tubular member 12 includes a first lumen 26 extending therethrough. Lumen 26 is configured to receive a needle 40 (FIG. 6). Lumen 26 preferably includes multiple (e.g., two) diameters along the length of tubular member 12. Thus, lumen 26 along first segment 14 of the percutaneous access device may have a diameter of about 10 Fr (3.3 mm) for receiving needle barrel portion 42. Lumen 26 may be transitioned along tapered portion 15 to a smaller second diameter along segment 16 of about 5.5. Fr (1.8 mm) for receiving end portion 44 of the needle. Those skilled in the art are capable of transitioning a lumen size utilizing conventional techniques during formation of the tubular member 12, e.g., such as forming the tubular member in a stepped or tapered mold sized for forming lumen 26.

One example of a needle 40 is shown in FIG. 6. In the example shown, needle 40 comprises barrel portion 42 and end portion 44 as described above. End portion 44 may taper to a piercing tip 45. Piercing tip 45 may have a beveled tip or other conventional piercing tip configuration. The proximal end portion of barrel 42 may have a Luer connection, external threads 43, or any other conventional structure that permits controlled movement of needle 40 in lumen 26. During such movement, the piercing tip 45 of needle 40 is selectively deployable, and retractable, from the distal end of tubular member 12.

Those skilled in the art will appreciate that numerous satisfactory means may be provided for deploying the piercing tip of needle 40 from lumen 26, and that the aforementioned Luer connection and threaded connection are only examples of such needle deployment structure. Non-limiting examples of known structures that may be employed for selectively deploying and retracting a needle tip from a tubular member are described, e.g., in U.S. Pat. Nos. 4,946,446; 5,374,250; 6,572,584; and 7,351,224, all incorporated by reference herein.

Figure 11:
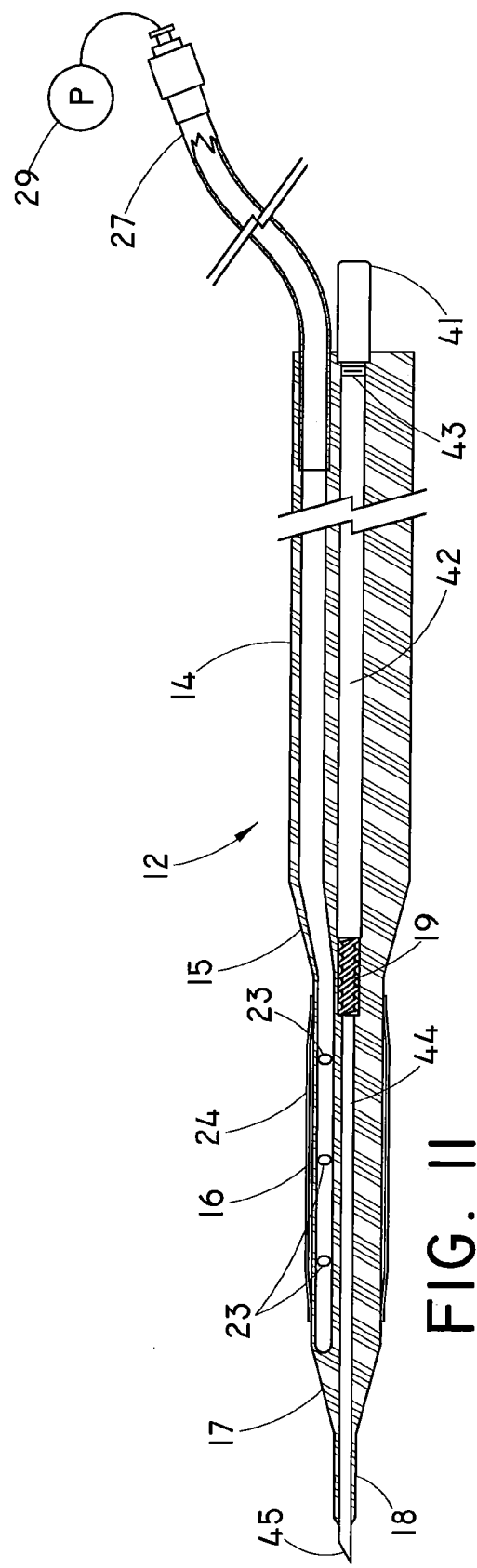
FIG. 11 is a side sectional view of a percutaneous access device similar to that of FIG. 2, including a biasing mechanism for selectively deploying and retracting the needle tip.

One example of a device including a mechanism for such deployment and retraction of the needle piercing tip is illustrated in FIG. 11. Other than including the deployment and retraction mechanism, FIG. 11 is similar to FIG. 2. Thus, common elements in the two figures are provided with the same reference numbers. Typically a deployment and retraction structure will include a biasing mechanism, such as spring 19 at or near the distal end, and a selectively activatable tip, or button, 41 for deploying the piercing tip 45, e.g., upon depressing the button. If desired, locking means can be provided such that the tip remains in the deployed position until the button is depressed a second time, resulting in the retraction of the piercing tip into lumen 26. Such mechanisms are well known, e.g., in the needle art, ballpoint pen art, etc., and further description of this feature is not necessary for an understanding of the operation of device 10.

As further shown in FIGS. 3-4, tubular member 12 includes a second lumen 28 extending partially therealong. Lumen 28 is configured for conveying a fluid under pressure for inflating the balloon 24. Lumen 28 is fluidly connected to a source of pressurized fluid 29 in well-known fashion, the fluid source 29 being indicated in the figures in only a general manner by the symbol "P". Those skilled in the art are well aware of suitable structure, connectors, etc., for fluidly connecting a fluid source with an internal surface, such as the interior of an inflatable balloon, and can readily arrange for suitable connection between fluid source 29 and lumen 28.

One or more side ports 23 are provided along tubular member second segment 16. Side ports 23 provide an opening between lumen 28 and the interior of balloon 24, to complete the fluid communication between fluid source 29 and the interior of balloon 24. The fluid provided by fluid source 29 may be a conventional fluid for such purposes, such as air, saline solution, or sterile water. The fluid may be supplied under a pressure of, e.g., about 5-15 atmospheres (507 to 1520 kPa), or other pressure adequate to dilate the tracheal wall upon inflation of balloon 24 to form a suitable opening in the tracheal wall. Those skilled in the art can readily optimize the parameters of an inflatable balloon to suit a particular purpose.

Tubular member 12 is preferably formed of conventional medical grade, synthetic materials used for such purposes in the medical arts, such as a polyamide, polyurethane, or polyethylene. Balloon 24 is preferably formed of flexible but inelastic materials such as PET or nylon. Those skilled in the art may readily optimize the compositions of tubular member 12 and balloon 24 based upon the intended use of access device 10.

FIG. 7 illustrates a tracheostomy tube 70 loaded onto percutaneous access device 10. As shown in the figures, tracheostomy tube 70 is loaded on tubular member first segment 14. In this instance, first segment 14 is in the nature of a loading dilator of a type described, e.g., in U.S. Pat. Nos. 5,653,230 and 7,036,510, both incorporated by reference herein. Tracheostomy tube 70 is typically composed of a medical grade, substantially rigid synthetic material, for example, radiopaque polyvinyl chloride. Tracheostomy tube 70 possesses a permanent curve which facilitates its introduction into an opening in the tracheal wall. When installed over first segment 14, the flexibility of tubular member 12 enables segment 14 to conform to the curve in the tracheostomy tube as shown in the figure. Tracheostomy tube 70 comprises a distal end 72 having an aperture open to the trachea and lungs of the patient when the device is in place along the tracheal wall, and includes an inflatable circumferential cuff 74 positioned adjacent to distal end 72 of tracheostomy tube 70. As is conventional, cuff 74 is desirably a thin wall, high volume, low pressure cuff, composed of a flexible and somewhat elastic material such as silicone, PET, polyurethane, and the like. This permits the cuff 74 to establish a good seal between the tracheostomy tube and the trachea of the patient upon insertion of the tracheostomy tube.

Tracheostomy tube 70 can further include a flange 76 for abutment against the skin of the patient when the tracheostomy tube is placed in the tracheal opening. Tracheostomy tube flanges are well known in the art and can comprise, for example, a flat disk or a conventional swivel neck plate that may be pivotable with respect to the body of the tracheostomy tube. A fluid reservoir 80 is provided to supply low-pressure fluid (such as air or saline) for inflating and deflating cuff 74, and a conventional tube or conduit 81 is provided to enable fluid communication between the cuff 74 and the fluid reservoir 80. The nature of such elements is well known and not critical to the present invention, and therefore will not be further described.

Tracheostomy tube 70 possesses conventional dimensions suited to the patient into whom it will be introduced. For example, for adult patients, the tracheostomy tube can typically have an outside diameter of about 8.5 to about 14.0 mm, and an inside diameter of about 6.0 to 10.0 mm. For pediatric patients, the tracheostomy tube can be made to any smaller dimensions as may be appropriate.

As indicated above, the purpose of forming an opening in the tracheal wall is to allow the insertion of tracheostomy tube 70 through the tracheal wall to establish an air passageway for the patient. Upon inflation, balloon 24 may have a diameter substantially the same as, or preferably greater than, the outside diameter of the tracheostomy tube 70 and the uninflated cuff 74 to facilitate insertion of the tracheostomy tube across the tracheal wall.

Thus, for example, for use with the tracheostomy tube 70 having an outside diameter of 12.0 mm, the balloon 24 should preferably have a diameter upon inflation when inflated of at least 12.0 mm, and preferably greater than this. As stated above, in one preferred embodiment, balloon has an inflated diameter of about 12.7 mm (38 French). This oversizing of the balloon diameter as compared to the tracheostomy tube diameter minimizes the possibility of damage to cuff 74 during insertion of tracheostomy tube 70 into the opening in the tracheal wall.

Figure 9:
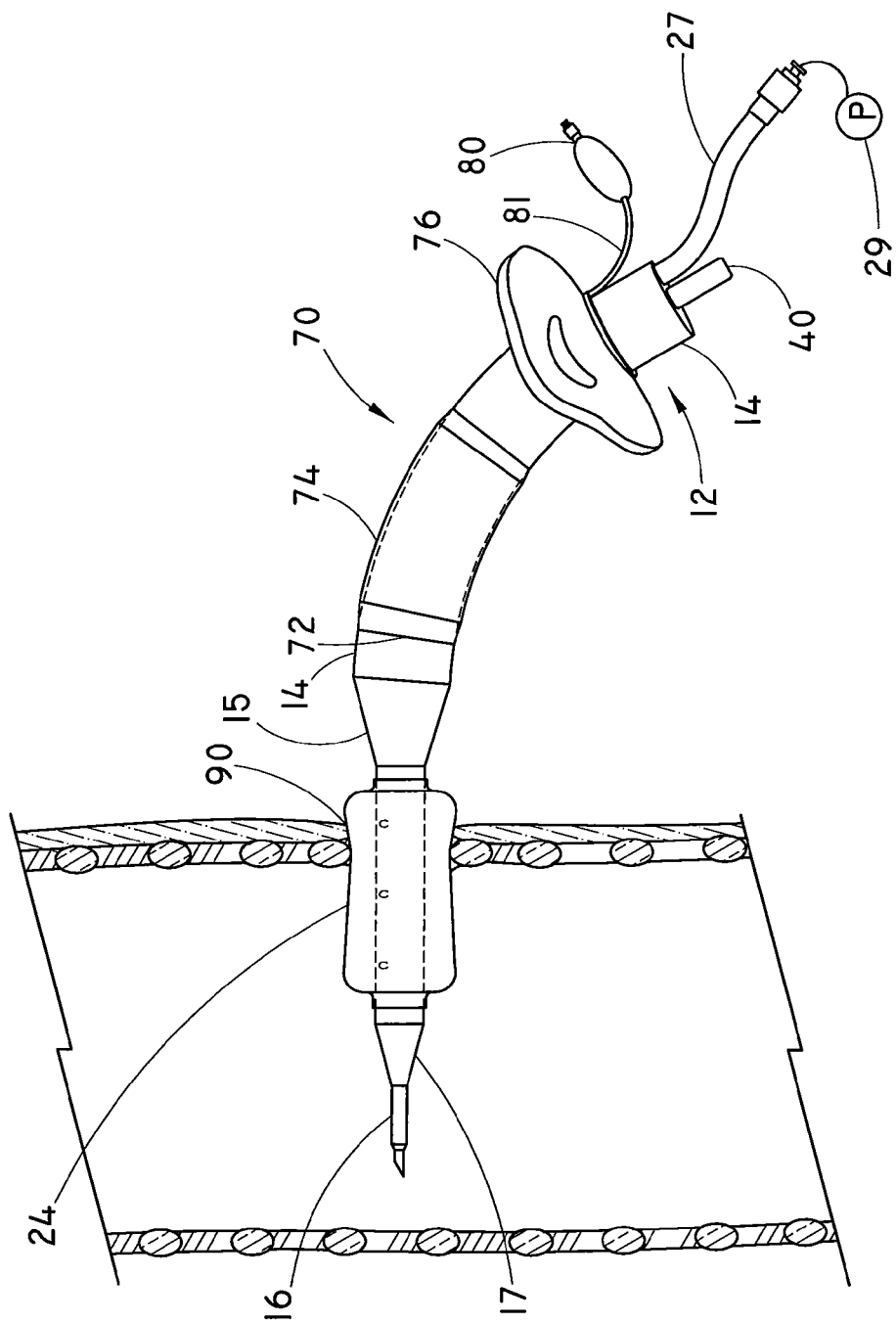
Figure 10:
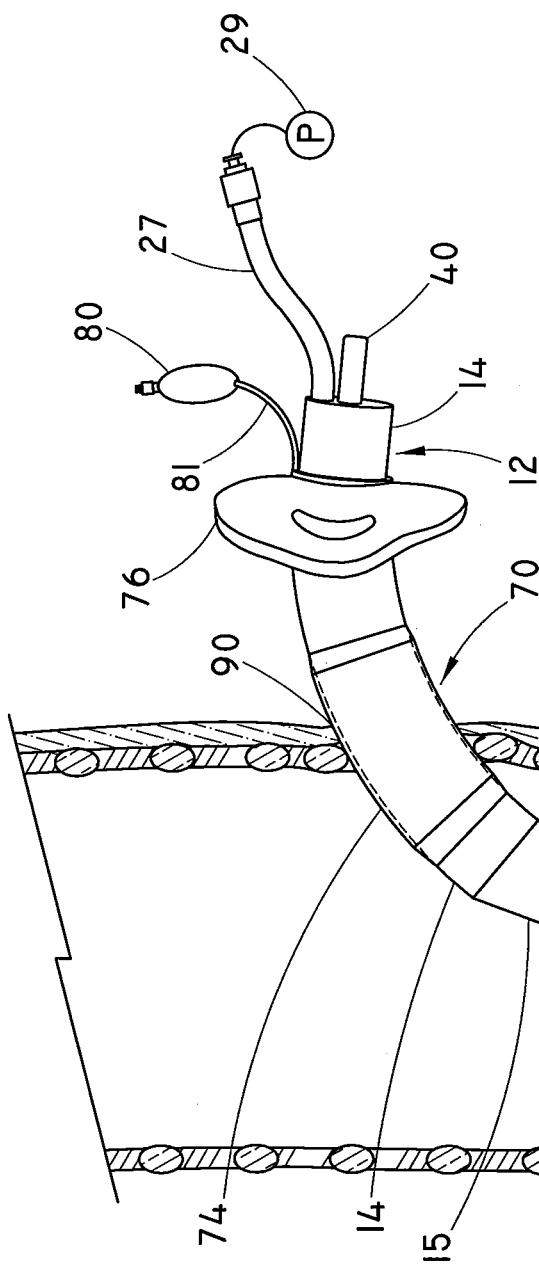

One example illustrating use of percutaneous access device 10 is shown in FIGS. 8-10. In this example, device 10 is used for forming an opening in the tracheal wall of a patient for placement of a tracheostomy tube.

Initially, the membrane of the tracheal wall is palpated in an appropriate area, such as between the first and second tracheal rings, or between the second and third tracheal rings. A slight incision may be made with a scalpel through the skin and the membrane. The distal end of percutaneous access device 10 is positioned at the opening, and the distal tip 45 of needle 40 is inserted through the tracheal wall at the incision. As a variation, some physicians may prefer to initially puncture the skin with the needle, and eliminate the incision step. The inventive device accommodates either of these techniques. Following insertion, the needle is retracted from the opening, and if desired, may be removed from device 10.

Following penetration of the tracheal wall by the needle, percutaneous access device 10 is advanced such that tapered portion 17 dilates the opening in the tracheal wall. Device 10 is further advanced until uninflated balloon 24 lies fully across the opening, as shown in FIG. 8. Prior to advancing device 10, the external surface of uninflated balloon 24 may be coated with copious amounts of a conventional, medical grade, water soluble lubricant to facilitate insertion.

The fluid supply 29 is then activated to provide pressurized fluid through conduit 27, and thereby through lumen 28 to inflate the balloon 24. Upon inflation of the balloon, the subcutaneous structures of the tracheal wall are atraumatically dilated in radial fashion, thereby forming opening 90 in the tracheal wall, as shown in FIG. 9.

Once opening 90 is formed, the balloon is deflated by evacuating the fluid therefrom in conventional manner, and device 10 is advanced in a downward direction into the trachea, as shown in FIG. 10. Alternatively, device 10 may be advanced with the balloon inflated, whereupon it is deflated after further advancement into the trachea. In either event, the presence of the lubricant on the outside of balloon 24 facilitates passage of the balloon through tracheal opening 90.

The tracheostomy tube 70 is positioned across the opening 90 by further advancing the device 10 until the flange 76 on the tracheostomy tube 70 abuts the skin over the tracheal opening 90. When the tracheostomy tube 70 is in proper position across the tracheal opening 90, it can be secured in place by suture and standard neck wrap in conventional fashion. Access device 10 is withdrawn through the lumen of tracheostomy tube 70 in a proximal direction, leaving the tracheostomy tube in position across the tracheal wall. The tracheal tube cuff 74 may now be inflated via fluid supply 80 establish a seal between the tracheostomy tube 70 and the interior of the tracheal wall of the patient in well-known fashion.

It is highly desirable that the fit of the tracheostomy tube 70 in the tracheal opening 90 be relatively tight. Of course, it is also desirable that the circumferential cuff 74 of the tracheostomy tube 70 not be damaged during its passage through the tracheal opening 90. Therefore, as stated, the method is preferably carried out with a balloon 24 whose diameter, when inflated, is equal to or slightly greater (e.g., about 1 mm greater) than the combined diameter of the tracheostomy tube 70 and the diameter of the uninflated cuff 74. The insertion of the tracheostomy tube 70 can also be aided by application of the lubricant to the outside of the tracheostomy tube 70 and cuff 74 before insertion.

Any undisclosed details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of ordinary skill in this art in view of the present disclosure.

The present invention is useful in the performance of surgical procedures, and will find applicability in human and veterinary medicine. In addition to providing a suitable opening in the tracheal wall for insertion of a tracheostomy tube as described, device 10 may also be utilized in other procedures, such as nephrostomy/cystostomy, biliary drainage, and the like. Those skilled in the art can readily determine appropriate uses based upon the present disclosure.

It is intended that the foregoing detailed description be regarded as illustrative rather than limiting, and that it be understood that it is the following claims, including all equivalents, that are intended to define the spirit and scope of this invention.

What is claimed is:

1. A device for providing access through a body wall of a patient to a target site, comprising:
   a hollow tubular member having a proximal end and a distal end, a first segment having a first diameter, and a second segment having a second diameter, said first diameter greater than said second diameter, a first distally tapered portion providing a transition between said first segment and said second segment, and a second distally tapered portion distal of said second segment, said hollow tubular member having a pair of lumens therealong, a first one of said lumens extending from a proximal portion of said tubular member to said distal end, and a second one of said lumens extending from a proximal portion of said tubular member to said second segment, at least one port along said second segment communicating with said second lumen;

an inflatable member disposed along said second segment at said at least one port, said inflatable member configured and arranged such that upon inflation thereof said inflatable member has a diameter at least as large as said first diameter; and wherein the first segment of the hollow tubular member comprises an outer surface configured to receive a tracheostomy tube.

2. The device of claim 1, comprising a conduit communicating with said second lumen for transmission of an inflation fluid through said second lumen and said at least one port to an interior of said inflatable member.

3. The device of claim 1, comprising a needle received in said first lumen, a distal tip of said needle selectively deployable from said distal end of said tubular member for piercing said body wall.

4. The device of claim 1, wherein said hollow tubular member further comprises a third segment having a third diameter, said second diameter greater than said third diameter, and wherein said second distally tapered portion provides a transition between said second segment and said third segment.

5. The device of claim 1, further comprising a medical device carried along said first segment.

6. The device of claim 5, wherein said medical device comprises a tracheostomy tube, and wherein said inflatable member is inflatable to a diameter at least as large as a diameter of the tracheostomy tube.

7. The device of claim 1, wherein said inflatable member is inflatable to a diameter exceeding the first diameter.

8. The device of claim 3, wherein said needle is selectively deployable and retractable from said tubular member distal end.

9. The device of claim 8, further comprising a biasing mechanism for selectively deploying and retracting said needle.

10. The device of claim 1, wherein said first diameter is about 26 French and said second diameter is about 14 French, and wherein said inflatable member is inflatable to a diameter of about 38 French.

11. An assembly for providing an airway through the tracheal wall of a patient, comprising:
a device for forming an opening in the tracheal wall, the device comprising a hollow tubular member having a proximal end and a distal end, a first segment having a first diameter, and a second segment having a second diameter, said first diameter greater than said second diameter, a first distally tapered portion providing a transition between said first segment and said second segment, and a second distally tapered portion distal of said second segment, said hollow tubular member having a pair of lumens therealong, a first lumen extending to said distal end, and a second lumen extending to said second segment, at least one port along said second segment communicating with said second lumen; an inflatable member disposed along said second segment at said at least one port, said inflatable member dimensioned such that upon inflation said inflatable member has a diameter at least as large as a diameter of a tracheostomy tube carried on said first segment;
a needle received in said first lumen, said needle having a piercing tip selectively deployable and retractable through said first lumen for piercing said tracheal wall; and
a tracheostomy tube carried on said first segment for positioning along said tracheal wall.

12. The assembly of claim 11, wherein said inflatable member comprises a balloon having a diameter upon inflation that exceeds a diameter of the tracheostomy tube.

13. The assembly of claim 12, wherein said hollow tubular member further comprises a third segment having a third diameter, said second diameter greater than said third diameter, and wherein said second distally tapered portion provides a transition between said second segment and said third segment.

14. The assembly of claim 11, further comprising a biasing mechanism for selectively deploying and retracting said needle.

15. The assembly of claim 11, comprising a conduit communicating with said second lumen for transmission of an inflation fluid through said second lumen and said at least one port to an interior of said inflatable member.

16. A method for providing an airway through the tracheal wall of a patient, comprising:
positioning an assembly at a site along the tracheal wall for insertion therethrough, the assembly comprising a hollow tubular member having a proximal end and a distal end, a first segment having a first diameter, and a second segment having a second diameter, the first diameter greater than the second diameter, a first distally tapered portion providing a transition between the first segment and the second segment, and a second distally tapered portion distal of the second segment, said hollow tubular member having a pair of lumens therealong, a first lumen extending from a proximal portion of said tubular member to said distal end, and a second lumen extending to said second segment, at least one port along the second segment communicating with the second lumen, a needle received in said first lumen such that a distal tip of said needle is selectively deployable from the distal end of the tubular member, an inflatable balloon disposed along the second segment and covering said at least one port, a conduit communicating with said second lumen for transmission of an inflation fluid through said second lumen and said at least one port to an interior of said inflatable balloon, and a tracheostomy tube carried by said first segment;
deploying said needle distal tip from said first lumen such that said needle tip pierces said tracheal wall at said site, thereby forming an opening to the trachea;
advancing the assembly along said opening such that said second distally tapered portion dilates the opening, and the balloon is positioned across the tracheal wall;
conveying an inflation fluid through said second lumen and said at least one port for inflating said balloon, such that said opening is dilated to a diameter of said balloon upon inflation;
advancing the assembly into the dilated opening such that the tracheostomy tube is positioned across the tracheal wall; and
withdrawing the hollow tubular member from the opening and the positioned tracheostomy tube.

17. The method of claim 16, further comprising the step of deflating the balloon prior to advancing the assembly into the dilated opening.

18. The method of claim 16, further comprising applying a lubricant to an outer surface of at least one of the balloon and tracheostomy tube.

19. The method of claim 16, wherein said hollow tubular member further comprises a third segment having a third diameter, said second diameter greater than said third diameter, and wherein said second distally tapered portion provides a transition between said second segment and said third segment, and wherein said needle distal tip is deployed through said third segment for piercing said tracheal wall.

20. The method of claim 16, wherein said balloon is inflatable to a diameter at least as large as a diameter of the tracheostomy tube.

\* \* \* \* \*